US012642558B2

(12) United States Patent
Nagaoka et al.

(10) Patent No.: US 12,642,558 B2
(45) Date of Patent: Jun. 2, 2026

(54) LEAD INTRODUCERS AND SYSTEMS AND METHODS INCLUDING THE LEAD INTRODUCERS

(71) Applicant: Boston Scientific Neuromodulation Corporation, Valencia, CA (US)

(72) Inventors: Eric Koji Nagaoka, Santa Clarita, CA (US); Ranjan Krishna Mukhari Nageri, Valencia, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 0 days.

(21) Appl. No.: 18/894,863

(22) Filed: Sep. 24, 2024

(65) Prior Publication Data

US 2025/0107822 A1 Apr. 3, 2025

Related U.S. Application Data

(60) Provisional application No. 63/542,064, filed on Oct. 2, 2023.

(51) Int. Cl.
*A61B 17/34* (2006.01)
*A61M 25/00* (2006.01)
(Continued)

(52) U.S. Cl.
CPC ..... *A61B 17/3468* (2013.01); *A61M 25/0097* (2013.01); *A61M 25/0102* (2013.01);
(Continued)

(58) Field of Classification Search
CPC ............ A61B 17/3417; A61B 17/3468; A61B 2017/347; A61N 1/0551; A61N 1/05;
(Continued)

(56) References Cited

U.S. PATENT DOCUMENTS 3,330,278 A 7/1967 Santomieri
3,359,978 A 12/1967 Smith
(Continued)

FOREIGN PATENT DOCUMENTS

EP 2008686 12/2008
WO 89/00436 1/1989
WO 03011361 2/2003

OTHER PUBLICATIONS

International Search Report and Wrtiten Opinion for PCT Application No. PCT/US2024/048181 mailed Nov. 19, 2024.

*Primary Examiner* — Katherine H Schwiker
(74) *Attorney, Agent, or Firm* — Branch Partners PLLC; Bruce E. Black

(57) ABSTRACT

A lead introducer includes a combined needle/sheath having a splittable sheath configured to split along the length of the splittable sheath, a splittable hub coupled to the proximal end region of the splittable sheath and configured to split into a first portion and a second portion, a needle defining a channel extending along the length of the needle for delivery of a lead through the needle, where the needle is not bonded to the splittable hub and the splittable sheath, and a non-cylindrical locking fixture attached to, or part of, a proximal end region of the needle, where the splittable hub includes a cavity having a shape complementary to the non-cylindrical locking fixture of the needle to hold the needle within the splittable hub and restrict rotation of the needle relative to the splittable hub. Another lead introducer includes a splittable hub and splittable needle attached to the splittable hub.

20 Claims, 8 Drawing Sheets

(51) Int. Cl.

| | | |
|---|---|---|
| *A61M 25/01* | (2006.01) | |
| *A61M 25/06* | (2006.01) | |
| *A61N 1/05* | (2006.01) | |
| A61B 17/00 | (2006.01) | |

(52) U.S. Cl.
CPC .................. *A61M 25/0668* (2013.01); *A61B 2017/00477* (2013.01); *A61B 2017/347* (2013.01); *A61N 1/05* (2013.01)

(58) Field of Classification Search
CPC .......... A61M 25/0668; A61M 25/0097; A61M 25/0102
See application file for complete search history.

(56) References Cited

U.S. PATENT DOCUMENTS

| | | | |
|---|---|---|---|
| 3,568,660 A | 3/1971 | Crites et al. | |
| 3,677,243 A | 7/1972 | Nerz | |
| 4,166,469 A | 9/1979 | Littleford | |
| 4,355,646 A | 10/1982 | Kallok et al. | |
| 4,449,973 A | 5/1984 | Luther | |
| RE31,855 E | 3/1985 | Osborne | |
| 4,512,351 A | 4/1985 | Pohndorf | |
| 4,608,986 A | 9/1986 | Beranek et al. | |
| 4,808,157 A | 2/1989 | Coombs | |
| 5,125,904 A | 6/1992 | Lee | |
| 5,255,691 A | 10/1993 | Otten | |
| 5,312,355 A | 5/1994 | Lee | |
| 5,320,602 A | 6/1994 | Karpiel | |
| 5,380,290 A | 1/1995 | Makower et al. | |
| 5,409,469 A | 4/1995 | Schaerf | |
| 5,441,504 A | 8/1995 | Pohndorf et al. | |
| 5,713,867 A | 2/1998 | Morris | |
| 5,741,233 A | 4/1998 | Riddle et al. | |
| 5,752,937 A | 5/1998 | Otten et al. | |
| 5,755,693 A | 5/1998 | Walker et al. | |
| 5,931,863 A | 8/1999 | Griffin, III et al. | |
| 6,080,141 A | 6/2000 | Castro et al. | |
| 6,181,969 B1 | 1/2001 | Gord | |
| 6,251,119 B1 | 6/2001 | Addis | |
| 6,358,460 B1 | 3/2002 | Hunt, Jr. et al. | |
| 6,454,744 B1 | 9/2002 | Spohn et al. | |
| 6,494,860 B2 | 12/2002 | Rocamora et al. | |
| 6,516,227 B1 | 2/2003 | Meadows et al. | |
| 6,582,390 B1 | 6/2003 | Sanderson | |
| 6,609,029 B1 | 8/2003 | Mann et al. | |
| 6,609,032 B1 | 8/2003 | Woods et al. | |
| 6,641,564 B1 | 11/2003 | Kraus | |
| 6,645,178 B1 | 11/2003 | Junker et al. | |
| 6,712,791 B2 | 3/2004 | Lui et al. | |
| 6,741,892 B1 | 5/2004 | Meadows et al. | |
| 6,749,600 B1 | 6/2004 | Levy | |
| 6,758,854 B1 | 7/2004 | Butler et al. | |
| 6,869,416 B2 | 3/2005 | Windheuser et al. | |
| 6,939,327 B2 | 9/2005 | Hall et al. | |
| 7,001,396 B2 | 2/2006 | Glazier et al. | |
| 7,014,626 B2 | 3/2006 | Sanderson | |
| 7,101,353 B2 | 9/2006 | Lui et al. | |
| 7,192,433 B2 | 3/2007 | Osypka et al. | |
| 7,244,150 B1 | 7/2007 | Brase | |
| 7,359,755 B2 | 4/2008 | Jones et al. | |
| 7,437,193 B2 | 10/2008 | Parramon | |
| 7,450,997 B1 | 11/2008 | Pianca et al. | |
| 7,524,305 B2 | 4/2009 | Moyer | |
| 7,672,734 B2 | 3/2010 | Anderson | |
| 7,744,571 B2 | 6/2010 | Fisher et al. | |
| 7,761,165 B1 | 7/2010 | He | |
| 7,783,359 B2 | 8/2010 | Meadows | |
| 7,792,590 B1 | 9/2010 | Pianca et al. | |
| 7,809,446 B2 | 10/2010 | Meadows | |
| 7,887,733 B2 | 2/2011 | Moyer | |
| 7,909,798 B2 | 3/2011 | Osypka | |
| 7,938,806 B2 | 5/2011 | Fisher et al. | |
| 7,941,227 B2 | 5/2011 | Barker | |
| 7,949,395 B2 | 5/2011 | Kuzma | |
| 7,974,706 B2 | 7/2011 | Moffitt et al. | |
| 7,985,232 B2 | 7/2011 | Potter et al. | |
| 7,993,305 B2 | 8/2011 | Ye et al. | |
| 8,043,263 B2 | 10/2011 | Helgeson et al. | |
| 8,105,287 B2 | 1/2012 | Fisher et al. | |
| 8,105,315 B2 | 1/2012 | Johnson et al. | |
| 8,112,159 B2 | 2/2012 | Harris et al. | |
| 8,137,317 B2 | 3/2012 | Osypka | |
| 8,147,456 B2 | 4/2012 | Fisher et al. | |
| 8,175,710 B2 | 5/2012 | He | |
| 8,180,461 B2 | 5/2012 | Mamo et al. | |
| 8,224,450 B2 | 7/2012 | Brase | |
| 8,271,094 B1 | 9/2012 | Moffitt et al. | |
| 8,273,059 B2 | 9/2012 | Nardeo et al. | |
| 8,295,944 B2 | 10/2012 | Howard et al. | |
| 8,348,899 B2 | 1/2013 | Chesnin et al. | |
| 8,364,278 B2 | 1/2013 | Pianca et al. | |
| 8,377,006 B2 | 2/2013 | Tal et al. | |
| 8,382,715 B2 | 2/2013 | Nardeo et al. | |
| 8,391,985 B2 | 3/2013 | McDonald | |
| 8,583,237 B2 | 11/2013 | Bedenbaugh | |
| 8,688,235 B1 | 4/2014 | Pianca et al. | |
| 8,831,742 B2 | 9/2014 | Pianca et al. | |
| 8,849,422 B2 | 9/2014 | Pianca | |
| 9,510,857 B2 | 12/2016 | Barker | |
| 9,931,109 B2 | 4/2018 | Burckhardt et al. | |
| 9,987,435 B2 | 6/2018 | Colantonio | |
| 11,529,510 B2 | 12/2022 | Leven | |
| 2002/0111617 A1 | 8/2002 | Cosman et al. | |
| 2003/0114899 A1 | 6/2003 | Woods et al. | |
| 2005/0021119 A1 | 1/2005 | Sage et al. | |
| 2005/0055027 A1 | 3/2005 | Yeung et al. | |
| 2005/0107861 A1 | 5/2005 | Harris et al. | |
| 2005/0113860 A1 | 5/2005 | Keidar | |
| 2007/0150036 A1 | 6/2007 | Anderson | |
| 2007/0276450 A1 | 11/2007 | Meadows et al. | |
| 2008/0300538 A1 | 12/2008 | Schweikert et al. | |
| 2009/0187222 A1 | 7/2009 | Barker | |
| 2009/0248111 A1 | 10/2009 | Pianca et al. | |
| 2009/0254019 A1 | 10/2009 | Gehl et al. | |
| 2009/0259283 A1 | 10/2009 | Brandt et al. | |
| 2009/0276021 A1 | 11/2009 | Meadows et al. | |
| 2010/0076535 A1 | 3/2010 | Pianca et al. | |
| 2010/0268298 A1 | 10/2010 | Moffit et al. | |
| 2011/0004267 A1 | 1/2011 | Meadows | |
| 2011/0005069 A1 | 1/2011 | Pianca | |
| 2011/0054402 A1 | 3/2011 | Tanabe et al. | |
| 2011/0078900 A1 | 4/2011 | Pianca et al. | |
| 2011/0130803 A1 | 6/2011 | McDonald | |
| 2011/0130816 A1 | 6/2011 | Howard et al. | |
| 2011/0130817 A1 | 6/2011 | Chen | |
| 2011/0130818 A1 | 6/2011 | Chen | |
| 2011/0218549 A1 | 9/2011 | Barker | |
| 2011/0224680 A1 | 9/2011 | Barker | |
| 2011/0224681 A1 | 9/2011 | McDonald | |
| 2011/0230893 A1 | 9/2011 | Barker | |
| 2011/0238129 A1 | 9/2011 | Moffitt et al. | |
| 2011/0313500 A1 | 12/2011 | Barker et al. | |
| 2012/0016378 A1 | 1/2012 | Pianca et al. | |
| 2012/0046710 A1 | 2/2012 | DiGiore et al. | |
| 2012/0071949 A1 | 3/2012 | Pianca et al. | |
| 2012/0165911 A1 | 6/2012 | Pianca | |
| 2012/0197375 A1 | 8/2012 | Pianca et al. | |
| 2012/0202928 A1 | 8/2012 | Barker et al. | |
| 2012/0203316 A1 | 8/2012 | Moffit et al. | |
| 2012/0203320 A1 | 8/2012 | DiGiore et al. | |
| 2012/0203321 A1 | 8/2012 | Moffit et al. | |
| 2012/0316615 A1 | 12/2012 | DiGiore et al. | |
| 2012/0323254 A1 | 12/2012 | Bonde et al. | |
| 2013/0053851 A1 | 2/2013 | Schmitz et al. | |
| 2013/0105071 A1 | 5/2013 | DiGiore et al. | |
| 2013/0197424 A1 | 8/2013 | Bedenbaugh | |
| 2013/0197602 A1 | 8/2013 | Pianca et al. | |
| 2013/0261684 A1 | 10/2013 | Howard | |
| 2013/0317587 A1 | 11/2013 | Barker | |
| 2013/0325091 A1 | 12/2013 | Pianca et al. | |
| 2014/0039586 A1 | 2/2014 | Barker et al. | |
| 2014/0039587 A1 | 2/2014 | Romero | |

(56)        References Cited

U.S. PATENT DOCUMENTS

| 2014/0073926 | A1 | 3/2014 | Rajendran et al. |
| 2014/0276927 | A1 | 9/2014 | Barker |
| 2014/0296953 | A1 | 10/2014 | Piaca et al. |
| 2014/0343647 | A1 | 11/2014 | Romero et al. |
| 2014/0353001 | A1 | 12/2014 | Romero et al. |
| 2014/0358207 | A1 | 12/2014 | Romero |
| 2014/0358209 | A1 | 12/2014 | Romero et al. |
| 2014/0358210 | A1 | 12/2014 | Howard et al. |
| 2015/0018915 | A1 | 1/2015 | Leven |
| 2015/0021817 | A1 | 1/2015 | Romero et al. |
| 2015/0045864 | A1 | 2/2015 | Howard |
| 2015/0066120 | A1 | 3/2015 | Govea |
| 2015/0073431 | A1 | 3/2015 | Barker |
| 2015/0073432 | A1 | 3/2015 | Barker |
| 2015/0151113 | A1 | 6/2015 | Govea et al. |
| 2016/0317800 | A1 | 11/2016 | Barker |
| 2017/0340891 | A1 | 11/2017 | Boggs et al. |
| 2018/0333173 | A1 | 11/2018 | Wang |
| 2020/0261714 | A1* | 8/2020 | Leven .................... A61N 1/372 |

* cited by examiner

LEAD INTRODUCERS AND SYSTEMS AND METHODS INCLUDING THE LEAD INTRODUCERS

CROSS-REFERENCE TO RELATED APPLICATIONS

This application claims the benefit under 35 U.S.C. § 119(e) of U.S. Provisional Patent Application Ser. No. 63/542,064, filed Oct. 2, 2023, which is incorporated herein by reference.

FIELD

The present invention is directed to the area of implantable stimulation systems and methods of making and using the systems. The present invention is also directed to a lead introducer for facilitating insertion of implantable stimulation leads into patients, as well as methods of making and using the lead introducers and stimulation leads.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

One aspect is a lead introducer including a combined needle/sheath having a splittable sheath having a length and a proximal end region and configured to split along the length of the splittable sheath into a first portion and a second portion, a splittable hub coupled to the proximal end region of the splittable sheath and configured to split into a first portion and a second portion, a needle having a length and a proximal end region, the needle defining a channel extending along the length of the needle for delivery of a lead through the needle, wherein the needle is configured to extend through the splittable hub and the splittable sheath, wherein the needle is not bonded to the splittable hub and the splittable sheath, and a non-cylindrical locking fixture attached to, or part of, the proximal end region of the needle, wherein the splittable hub includes a cavity having a shape complementary to the non-cylindrical locking fixture of the needle to hold the needle within the splittable hub and restrict rotation of the needle relative to the splittable hub.

In at least some aspects, the non-cylindrical locking fixture includes at least one wing. In at least some aspects, the combined needle/sheath further includes a splittable luer configured for insertion into the splittable hub to lock the non-cylindrical locking fixture of the needle within the cavity of the splittable hub, wherein the splittable luer is configured to split into a first portion and a second portion. In at least some aspects, the needle is not bonded to the splittable luer. In at least some aspects, the splittable hub and the splittable luer include complementary locating features to facilitate simultaneous splitting of the splittable hub and the splittable luer.

Another aspect is a lead introducer that includes a combined needle/sheath having a splittable sheath having a length and a proximal end region and configured to split along the length of the splittable sheath into a first portion and a second portion, a splittable hub coupled to the proximal end region of the splittable sheath and configured to split into a first portion and a second portion, a needle having a length and a proximal end region, the needle defining a channel extending along the length of the needle for delivery of a lead through the needle, wherein the needle is configured to extend through the splittable hub and the splittable sheath, wherein the needle is not bonded to the splittable hub and the splittable sheath, and a splittable luer configured for insertion into the splittable hub and adhesively bonded to the needle, wherein the splittable luer is configured to split into a first portion and a second portion breaking the adhesive bond between at least one of the first or second portions of the splittable luer and the needle.

In at least some aspects, the splittable hub and the splittable luer include complementary locating features to facilitate simultaneous splitting of the splittable hub and the splittable luer. In at least some aspects, the splittable hub includes a body and at least two tabs extending from the body, wherein the splittable hub is configured to be split, along with the splittable sheath and the splittable luer, using the at least two tabs.

In at least some aspects of any of the lead introducers described above, the needle defines a slot along the length of the needle configured for lateral release of the lead from the channel of the needle. In at least some aspects of any of the lead introducers described above, the first portion of the splittable sheath is permanently attached to the first portion of the hub so that when the hub is split into the first and second portions, the first portion of the splittable sheath remains attached to the first portion of the hub.

Yet another aspect is a lead introducer that includes a splittable hub configured to split into a first portion and a second portion; and a splittable needle coupled to the splittable hub and having a length and a proximal end region, the splittable needle defining a channel extending along the length of the splittable needle for delivery of a lead through the splittable needle, wherein the splittable needle includes at least one seam and is configured to split, along with the splittable hub, along the at least one seam into a first portion and a second portion.

In at least some aspects, the splittable needle is perforated, etched, stamped, scored, or grooved along the at least one seam to facilitate splitting of the splittable needle. In at least some aspects, the splittable needle includes two portions that are tack or spot welded along the at least one seam for temporary joining of the two portions. In at least some aspects, the lead introducer further includes a fluid-resistant coating or liner disposed over at least a portion of an interior or exterior surface of the splittable needle. In at least some aspects, the fluid-resistant coating or liner is disposed over at least a portion of the at least one seam of the splittable needle.

In at least some aspects of any of the lead introducers described above, the splittable hub includes a body and at least two tabs extending from the body, wherein the splittable hub is configured to be split, along with the splittable sheath, using the at least two tabs. In at least some aspects of any of the lead introducers described above, the lead introducer further includes a stylet configured for insertion into the channel of the needle. In at least some aspects of any of the lead introducers described above, the splittable hub includes at least one slit or weakened region for splitting the splittable hub into the first and second portions.

A further aspects is an insertion kit that includes any of the lead introducers described above; and a lead configured for implantation into a patient, the lead having a lead body having a distal end portion and a proximal end portion, a plurality of electrodes disposed at the distal end portion of the lead body, a plurality of terminals disposed at the proximal end portion of the lead body, and a plurality of conductive wires coupling the electrodes electrically to the terminals; wherein the lead is insertable through the channel of the needle.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein:

FIG. 4D is a schematic end view of the splittable hub of the combined needle/sheath of the lead introducer of FIG. 3A;

FIG. 4E is a schematic perspective view of the splittable luer of the combined needle/sheath of the lead introducer of FIG. 3A;

DETAILED DESCRIPTION

The present invention is directed to the area of implantable stimulation systems and methods of making and using the systems. The present invention is also directed to a lead introducer for facilitating insertion of implantable stimulation leads into patients, as well as methods of making and using the lead introducers and stimulation leads.

Suitable implantable electrical stimulation systems include, but are not limited to, a least one lead with one or more electrodes disposed along a distal end of the lead and one or more terminals disposed along the one or more proximal ends of the lead. Examples of electrical stimulation systems with leads are found in, for example, U.S. Pat. Nos. 6,181,969; 6,295,944; 6,391,985; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,831,742; 8,688,235; 6,175,710; 6,224,450; 6,271,094; 6,295,944; 6,364,278; and 6,391,985; U.S. Patent Application Publications Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; 2011/0005069; 2010/0268298; 2011/0130817; 2011/0130818; 2011/0078900; 2011/0238129; 2011/0313500; 2012/0016378; 2012/0046710; 2012/0165911; 2012/0197375; 2012/0203316; 2012/0203320; and 2012/0203321, all of which are incorporated by reference in their entireties. It will be understood that the lead introducers described herein can also be used for implantation of other types of leads including, but not limited to, optical or electrical/optical leads.

Figure 1:
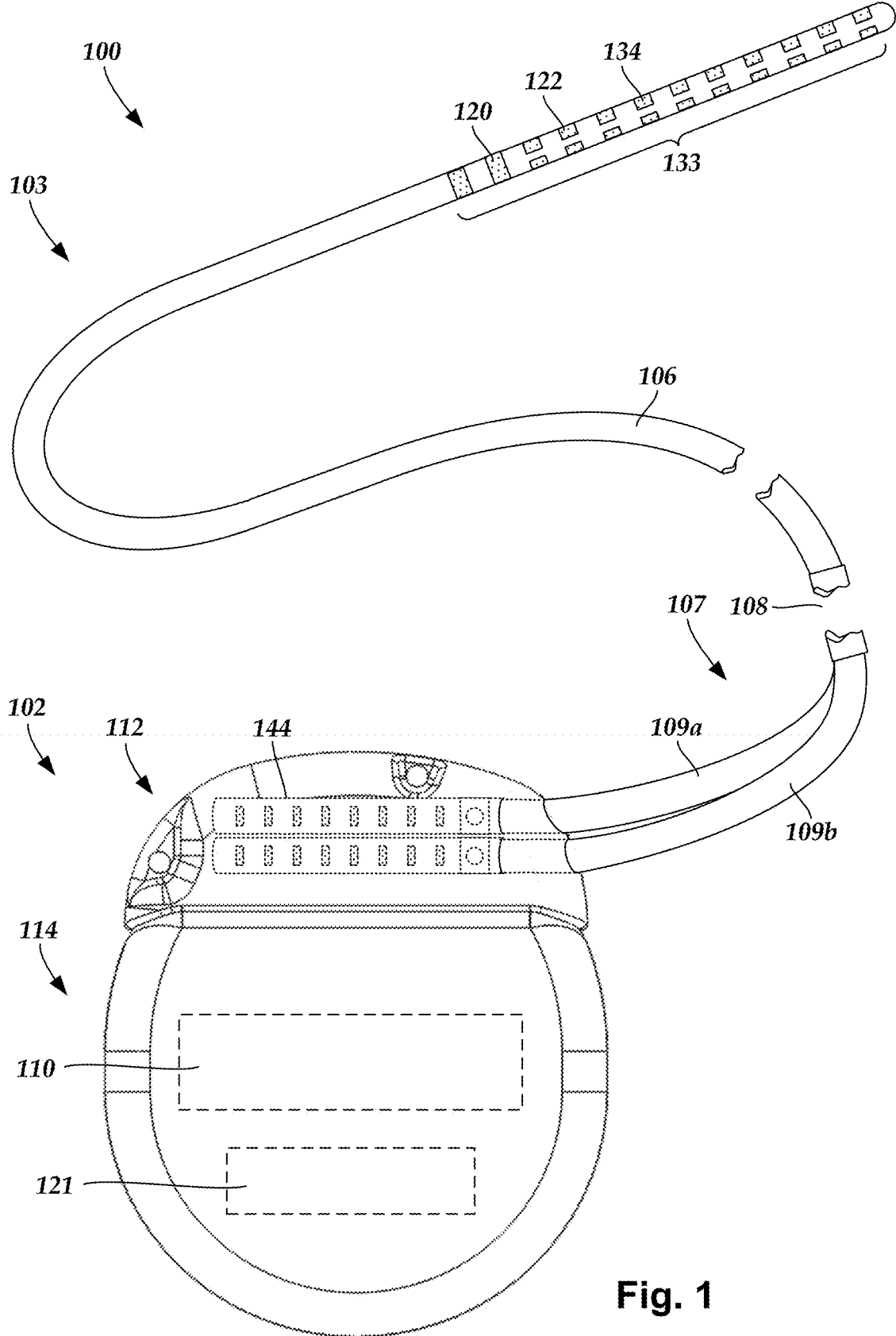
FIG. 1 is a schematic view of another embodiment of an electrical stimulation system that includes a percutaneous lead body coupled to a control module.

FIG. 1 illustrates schematically one embodiment of an electrical stimulation system 100. The electrical stimulation system includes a control module (e.g., a stimulator or pulse generator, such as an implantable pulse generator or an external test generator) 102 and at least one lead 103 coupleable to the control module 102. The lead 103 includes one or more lead bodies 106, an array of electrodes 133, such as electrode 134, and an array of terminals (e.g., 210 in FIGS. 2A and 2B) disposed along the one or more lead bodies 106. In at least some embodiments, the lead is isodiametric along a longitudinal length of the lead body 106. FIG. 1 illustrates one lead 103 coupled to a control module 102. Other embodiments may include two, three, four, or more leads 103 coupled to the control module 102.

The lead 103 can be coupled to the control module 102 in any suitable manner. In at least some embodiments, the lead 103 couples directly to the control module 102. In at least some other embodiments, the lead 103 couples to the control module 102 via one or more intermediate devices. For example, in at least some embodiments one or more lead extensions 224 (see e.g., FIG. 2B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

In FIG. 1, the electrical stimulation system 100 is shown having a splitter 107 configured and arranged for facilitating coupling of the lead 103 to the control module 102. The splitter 107 includes a splitter connector 108 configured to couple to a proximal end of the lead 103, and one or more splitter tails 109a and 109b configured and arranged to couple to the control module 102 (or another splitter, a lead extension, an adaptor, or the like).

The control module 102 typically includes a connector housing 112 and a sealed electronics housing 114. An electronic subassembly 110 and an optional power source 121 are disposed in the electronics housing 114. A control module connector 144 is disposed in the connector housing 112. The control module connector 144 is configured and arranged to make an electrical connection between the lead 103 and the electronic subassembly 110 of the control module 102.

The electrical stimulation system or components of the electrical stimulation system, including one or more of the lead bodies 106 and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium. The number of electrodes 134 in each array 133 may vary. For example, there can be two, four, six, eight, ten, twelve, fourteen, sixteen, or more electrodes 134. As will be recognized, other numbers of electrodes 134 may also be used.

The electrodes of the one or more lead bodies 106 are typically disposed in, or separated by, a non-conductive, biocompatible material such as, for example, silicone, polyurethane, polyetheretherketone ("PEEK"), epoxy, and the like or combinations thereof. The lead bodies 106 may be formed in the desired shape by any process including, for example, molding (including injection molding), casting, and the like. The non-conductive material typically extends from the distal end of the one or more lead bodies 106 to the proximal end of each of the one or more lead bodies 106.

Figure 2A:
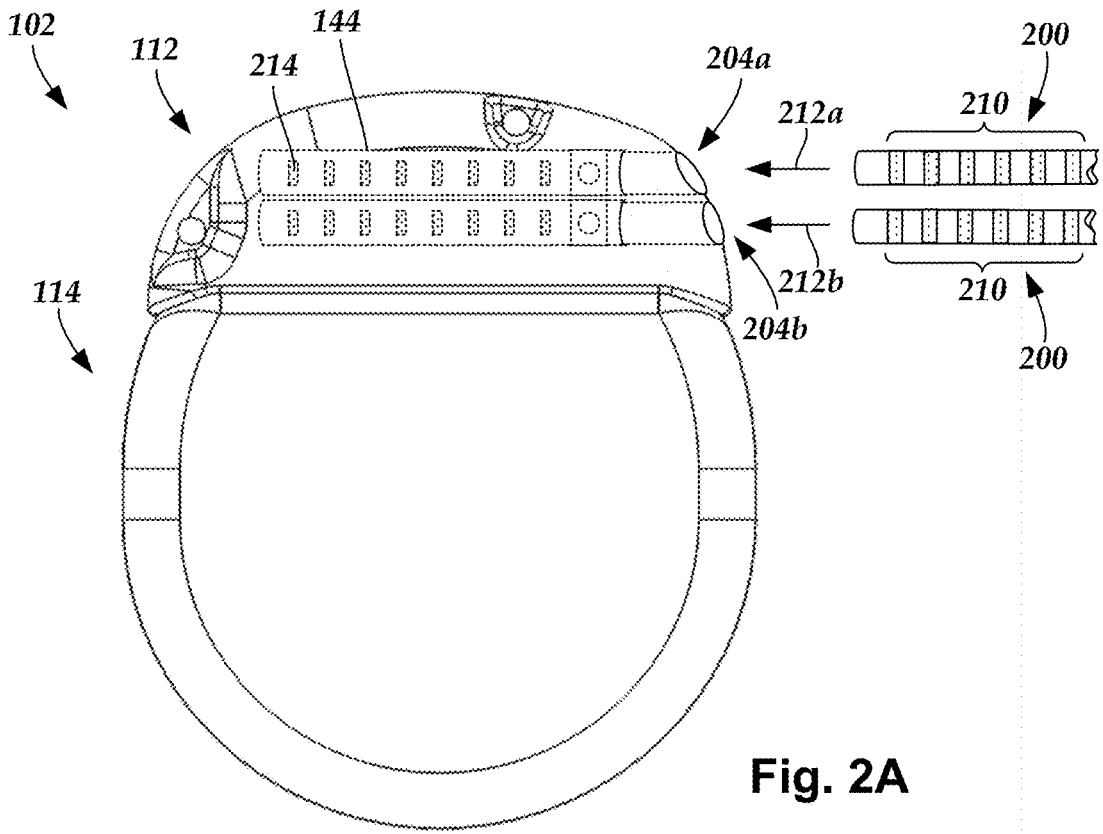
FIG. 2A is a schematic view of one embodiment of a plurality of connector assemblies disposed in the control module of FIG. 1, the connector assemblies configured to receive the proximal portions of the lead bodies of FIG. 1.
Figure 2B:
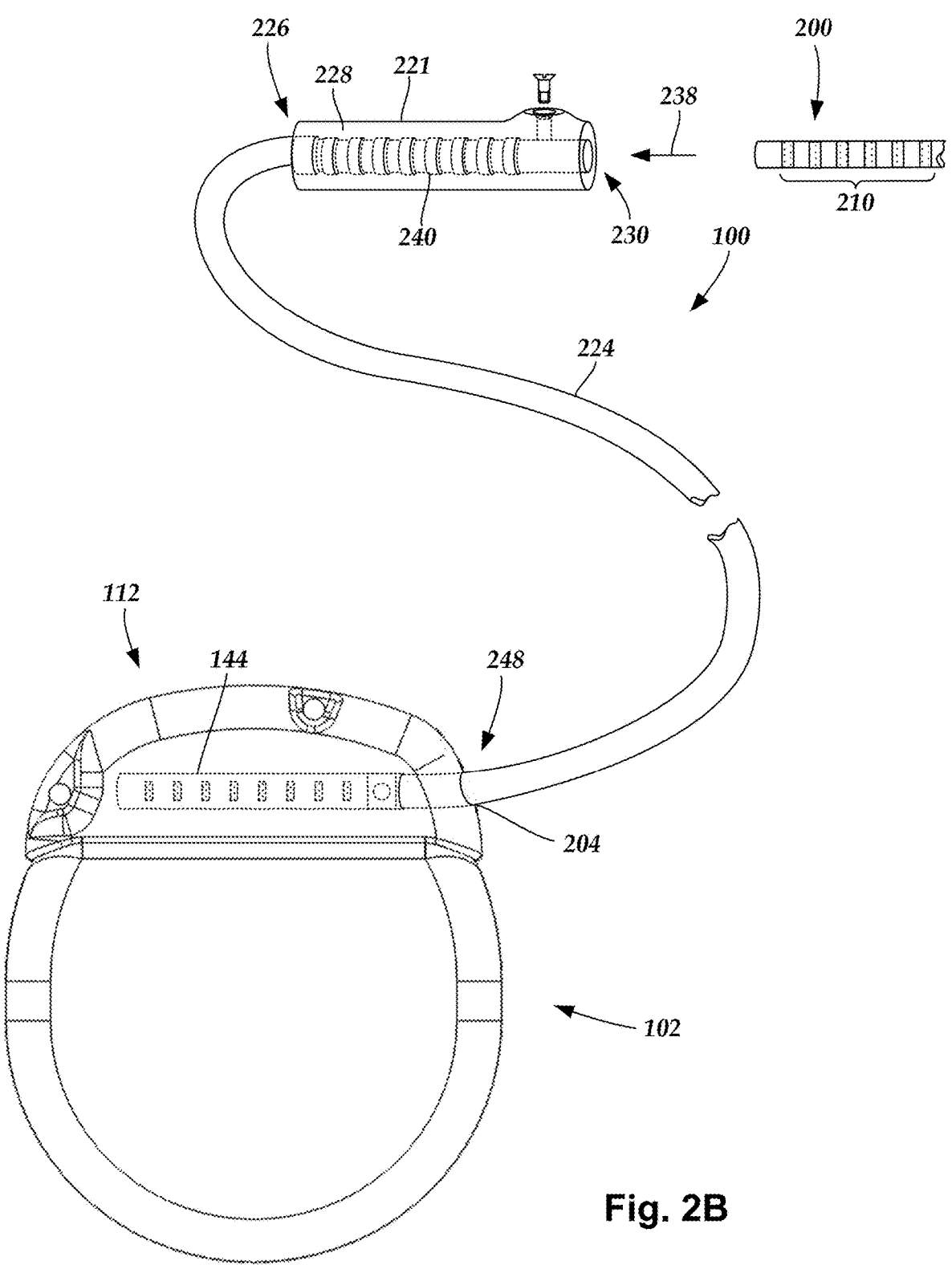
FIG. 2B is a schematic view of one embodiment of a proximal portion of the lead body of FIG. 1, a lead extension, and the control module of FIG. 1, the lead extension configured to couple the lead body to the control module.

Terminals (e.g., 210 in FIGS. 2A and 2B) are typically disposed along the proximal end of the one or more lead bodies 106 of the electrical stimulation system 100 (as well as any splitters, lead extensions, adaptors, or the like) for electrical connection to corresponding connector contacts (e.g., 214 in FIG. 2A and 240 in FIG. 2B). The connector contacts are disposed in connectors (e.g., 144 in FIGS. 1-2B; and 221 in FIG. 2B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the lead body 106, for example, for inserting a stylet to facilitate placement of the lead body 106 within a body of a patient. Additionally, there may be one or more lumens (not shown) that open at, or near, the distal end of the lead body 106, for example, for infusion of drugs or medication into the site of implantation of the one or more lead bodies 106. In at least one embodiment, the one or more lumens are flushed continually, or on a regular basis, with saline, epidural fluid, or the like. In at least some embodiments, the one or more lumens are permanently or removably sealable at the distal end.

FIG. 2A is a schematic side view of one embodiment of a proximal end of one or more elongated devices 200 configured and arranged for coupling to one embodiment of the control module connector 144. The one or more elongated devices may include, for example, the lead body 106, one or more intermediate devices (e.g., the splitter 107 of FIG. 1, the lead extension 224 of FIG. 2B, an adaptor, or the like or combinations thereof), or a combination thereof. FIG. 2A illustrates two elongated devices 200 coupled to the control module 102. These two elongated devices 200 can be two tails as illustrated in FIG. 1 or two different leads or any other combination of elongated devices.

The control module connector 144 defines at least one port into which a proximal end of the elongated device 200 can be inserted, as shown by directional arrows 212a and 212b. In FIG. 2A (and in other figures), the connector housing 112 is shown having two ports 204a and 204b. The connector housing 112 can define any suitable number of ports including, for example, one, two, three, four, five, six, seven, eight, or more ports.

The control module connector 144 also includes a plurality of connector contacts, such as connector contact 214, disposed within each port 204a and 204b. When the elongated device 200 is inserted into the ports 204a and 204b, the connector contacts 214 can be aligned with a plurality of terminals 210 disposed along the proximal end(s) of the elongated device(s) 200 to electrically couple the control module 102 to the electrodes (134 of FIG. 1) disposed at a distal end of the lead 103.

Examples of connectors in control modules are found in, for example, U.S. Pat. Nos. 7,244,150 and 8,224,450, which are incorporated by reference in their entireties.

FIG. 2B is a schematic side view of another embodiment of the electrical stimulation system 100. The electrical stimulation system 100 includes a lead extension 224 that is configured and arranged to couple one or more elongated devices 200 (e.g., the lead body 106, the splitter 107, an adaptor, another lead extension, or the like or combinations thereof) to the control module 102. In FIG. 2B, the lead extension 224 is shown coupled to a single port 204 defined in the control module connector 144. Additionally, the lead extension 224 is shown configured and arranged to couple to a single elongated device 200. In alternate embodiments, the lead extension 224 is configured and arranged to couple to multiple ports 204 defined in the control module connector 144, or to receive multiple elongated devices 200, or both.

A lead extension connector 221 is disposed on the lead extension 224. In FIG. 2B, the lead extension connector 221 is shown disposed at a distal end 226 of the lead extension 224. The lead extension connector 221 includes a connector housing 228. The connector housing 228 defines at least one port 230 into which terminals 210 of the elongated device 200 can be inserted, as shown by directional arrow 238. The connector housing 228 also includes a plurality of connector contacts, such as connector contact 240. When the elongated device 200 is inserted into the port 230, the connector contacts 240 disposed in the connector housing 228 can be aligned with the terminals 210 of the elongated device 200 to electrically couple the lead extension 224 to the electrodes (134 of FIG. 1) disposed along the lead (103 in FIG. 1).

In at least some embodiments, the proximal end of the lead extension 224 is similarly configured and arranged as a proximal end of the lead 103 (or other elongated device 200). The lead extension 224 may include a plurality of electrically conductive wires (not shown) that electrically couple the connector contacts 240 to a proximal end 248 of the lead extension 224 that is opposite to the distal end 226. In at least some embodiments, the conductive wires disposed in the lead extension 224 can be electrically coupled to a plurality of terminals (not shown) disposed along the proximal end 248 of the lead extension 224. In at least some embodiments, the proximal end 248 of the lead extension 224 is configured and arranged for insertion into a connector disposed in another lead extension (or another intermediate device). In other embodiments (and as shown in FIG. 2B), the proximal end 248 of the lead extension 224 is configured and arranged for insertion into the control module connector 144.

Returning to FIG. 1, at least some of the stimulation electrodes take the form of segmented electrodes that extend only partially around the perimeter (for example, the circumference) of the lead. These segmented electrodes can be provided in sets of electrodes, with each set having electrodes circumferentially distributed about the lead at a particular longitudinal position.

In at least some embodiments, a practitioner may determine the position of the target neurons using recording electrode(s) and then position the stimulation electrode(s) accordingly. In some embodiments, the same electrodes can be used for both recording and stimulation. In some embodiments, separate leads can be used; one with recording electrodes which identify target neurons, and a second lead with stimulation electrodes that replaces the first after target neuron identification. In some embodiments, the same lead may include both recording electrodes and stimulation electrodes or electrodes may be used for both recording and stimulation.

In FIG. 1, the electrodes 134 are shown as including both ring electrodes 120 and segmented electrodes 122. In some embodiments, the electrodes 134 are all segmented. The segmented electrodes 122 of FIG. 1 are in sets of three (one of which is not visible in FIG. 1), where the three segmented electrodes of a particular set are electrically isolated from one another and are circumferentially offset along the lead 1-3. Any suitable number of segmented electrodes can be formed into a set including, for example, two, three, four, or more segmented electrodes. The lead 103 of FIG. 1 has thirty segmented electrodes 122 (ten sets of three electrodes each) and two ring electrodes 120 for a total of 32 electrodes 134.

Segmented electrodes can be used to direct stimulus current to one side, or even a portion of one side, of the lead. When segmented electrodes are used in conjunction with an implantable pulse generator that delivers current stimulus, current steering can be achieved to more precisely deliver the stimulus to a position around an axis of the lead (i.e., radial positioning around the axis of the lead). Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a segmented electrode array, current steering can be performed not only along a length of the lead but also around a perimeter of the lead. This provides precise three-dimensional targeting and delivery of the current stimulus to neural target tissue, while potentially avoiding stimulation of other tissue.

Examples of leads with segmented electrodes include U.S. Patent Application Publications Nos. 2010/0268298; 2011/0005069; 2011/0078900; 2011/0130803; 2011/0130816; 2011/0130817; 2011/0130818; 2011/0078900; 2011/0238129; 2011/0313500; 2012/0016378; 2012/0046710; 2012/0071949; 2012/0165911; 2012/0197375; 2012/0203316; 2012/0203320; 2012/0203321; 2013/0197602; 2013/0261684; 2013/0325091; 2013/0317587; 2014/0039587; 2014/0353001; 2014/0358209; 2014/0358210; 2015/0018915; 2015/0021817; 2015/0045864; 2015/0021817; 2015/0066120; 2013/0197424; 2015/0151113; 2014/0358207; and U.S. Pat. No. 8,483,237, all of which are incorporated herein by reference in their entireties. A lead may also include a tip electrode and examples of leads with tip electrodes include at least some of the previously cited references, as well as U.S. Patent Application Publications Nos. 2014/0296953 and 2014/0343647, all of which are incorporated herein by reference in their entireties. A lead with segmented electrodes may be a directional lead that can provide stimulation in a particular direction using the segmented electrodes.

Conventional percutaneous implantation techniques often include inserting a lead introducer, such as an epidural needle, into a patient. A lead is then inserted into the lead introducer and the lead introducer is positioned at a target stimulation location. When the lead is correctly positioned, the lead introducer is removed from the patient, leaving the lead in place. Often the lead introducer is removed from the patient by sliding the lead introducer off the proximal end of the lead. This action, however, may result in movement of the lead so that it is no longer positioned at the desired stimulation location.

Other percutaneous implantation techniques utilize a lateral release lead introducer that includes a multi-piece insertion needle that enables a lead to be laterally separated from the multi-piece insertion needle instead of sliding the needle off the end of the lead. Lateral release can reduce inadvertent movement of the lead as the lead introducer is removed. Lateral release lead introducers can be particularly useful for implanting leads that have multiple tails, such as the lead 103 illustrated in FIG. 3, or other non-isodiametric arrangements along the lead. Examples of lateral release lead introducers are found in, for example, U.S. Pat. Nos. 10,226,616 and 11,529,510 and U.S. Patent Application Publications Nos. 2011/0224680, 2014/0039586, 2014/0276927, 2015/0073431, 2015/0073432, 2016/0317800, and 2018/0333173, all of which are incorporated herein by reference in their entireties.

At least some of these lateral release lead introducers include an outer needle, an inner needle, a splittable member, and a stylet. The four components of these lateral release lead introducers introduce more complexity than the conventional lead introducer discussed above which only uses one or two components (e.g., an epidural needle and an optional stylet). In some instances, these earlier lateral release lead introducers are less stiff than desired, which may hinder, or lengthen the duration of, insertion.

To reduce the number of components and complexity, FIGS. 3A to 3D illustrate a two component lateral release lead introducer 430 having a combined needle/sheath 440 and a stylet 442. The stylet 442 includes a shaft 442a and a handle 442b. The shaft 442a of the stylet 442 is inserted into the combined needle/sheath 440 and the combination is inserted into the patient. After insertion and location of the lead introducer 430 at or near the implant site, the stylet 442 is removed from the combined needle/sheath 440 and a lead 103 is inserted into the combined needle/sheath 440 for delivery and placement of the lead at the implant site.

In at least some embodiments, the combined needle/sheath 440 includes a splittable sheath 446, a splittable hub 444 attached to the splittable sheath, and a needle 448 that is locked into, but not bonded to, the splittable hub or the splittable sheath. The combined needle/sheath 440 can also include a splittable luer 454 that can be partially inserted into the splittable hub 444 for retention of a proximal portion 445 of the needle 448 within the splittable hub. Any other suitable mechanism or component can be used to retain the proximal portion of the needle 448 within the splittable hub 444. In at least some embodiments, the splittable sheath 446 is bonded to the splittable hub 444. For example, the splittable hub 444 can be molded onto the splittable sheath 446 or the splittable sheath can be adhesively attached to the splittable hub.

The splittable sheath 446 is arranged to split along the longitudinal length of the splittable sheath into two portions for removal of the splittable sheath after placement of the lead. In at least some embodiments, the splittable sheath 446 includes one or more perforated (or scored, weakened, thinned, or the like) regions 474 extending along at least a portion of the longitudinal length of the splittable sheath 446. In at least some embodiments, the splittable sheath 446 can be pre-split, perforated, scored, weakened, or thinned only within, or adjacent to, the hub 444 and have no further perforations or the like along the length of the splittable sheath. The splittable sheath can be made of any suitable material including, but not limited to, polymer materials such as high density polyethylene (HDPE), polytetrafluoroethylene (PTFE), or the like. As an example, materials such as PTFE, when extruded, can split easily and reliably in the direction of the extrusion without having to pre-score or perforate.

FIGS. 3D and 4A to 4E illustrate proximal portions of the splittable sheath 446, splittable hub 444, and splittable luer 454. The splittable hub 444 includes a body 462 and at least two pull-apart tabs 464, 466 that extend away from the body 462 of the splittable hub. The two pull-apart tabs 464, 466 can be used to separate each of the splittable sheath 446, the splittable hub 444, and the splittable luer 454 into two portions by pulling the two pull-apart tabs away from each other. In some embodiments, the separation process may also include first squeezing the two pull-apart tabs 464, 466 together to initiate separation of one or both of the splittable hub 444 and splittable sheath 446 and then pulling the two pull-apart tabs 464, 466 away from each other to complete the separation.

In at least some embodiments, an angle 468 between the two pull-apart tabs 464, 466 is no more than 180, 120, 90, 60, 30, or 20 degrees. In other embodiments, the pull-apart tabs can be 180 degrees apart, as disclosed in U.S. Patent Application Publication Nos. 2011/0224680, 2014/0039586, 2014/0276927, 2015/0073431, and 2015/0073432, all of which are incorporated herein by reference in their entireties. In yet other embodiments, the pull-apart tabs may extend proximally parallel (or at an acute angle no more than 89, 80, 75, 60, or 45 degrees) to the longitudinal axis of the splittable sheath 450 as disclosed in U.S. Patent Application Publication No. 2016/0317800, incorporated herein by reference in its entirety.

In at least some embodiments, the splittable hub 444 and the splittable luer 454 can include one or two slits or weakened regions 463a, 463b, 463c, and 463d between the pull-apart tabs 464, 466. These slits or weakened regions 463a, 463b, 463c, and 463d facilitate separation of the splittable hub 444 and the splittable luer 454 into two portions when the splittable sheath 446 is split and separated into two regions using the two pull-apart tabs 464, 466, as described above. In at least some embodiments, one or more of the slits or weakened regions 463a, 463b, 463c, and 463d are a V-shaped with an apex toward the center of the splittable hub 444 or the splittable luer 454, as illustrated, for example, in FIGS. 4D and 4E. In at least some embodiments, the portion of the splittable hub 444 or splittable luer 454 with the slits or weakened regions 463a, 463b, 463c, and 463d is shorter in length than other portions of the splittable hub or splittable luer. In the illustrated embodiments of FIGS. 3A to 4E, the slits or weakened regions 463a, 463b of the splittable hub 444 only extend partially along the length of the splittable hub with the remainder of the length of this portion of the splittable hub being open. This reduces the length of the splittable hub 444 that is split in order to the separate the splittable hub into two portions.

After inserting the lead and positioning the lead at the desired implant position, the splittable sheath 446, splittable hub 444, and splittable luer 454 can be split simultaneously into two parts each using the two pull-apart tabs 464, 466. The resulting split parts of the splittable sheath 446, splittable hub 444, and splittable luer 454 can be withdrawn from around the needle and, in the case of the splittable sheath, from the patient tissue. These parts can be discarded leaving the needle 448 and the lead.

Figures 3A, 3B, 3C, 3D:
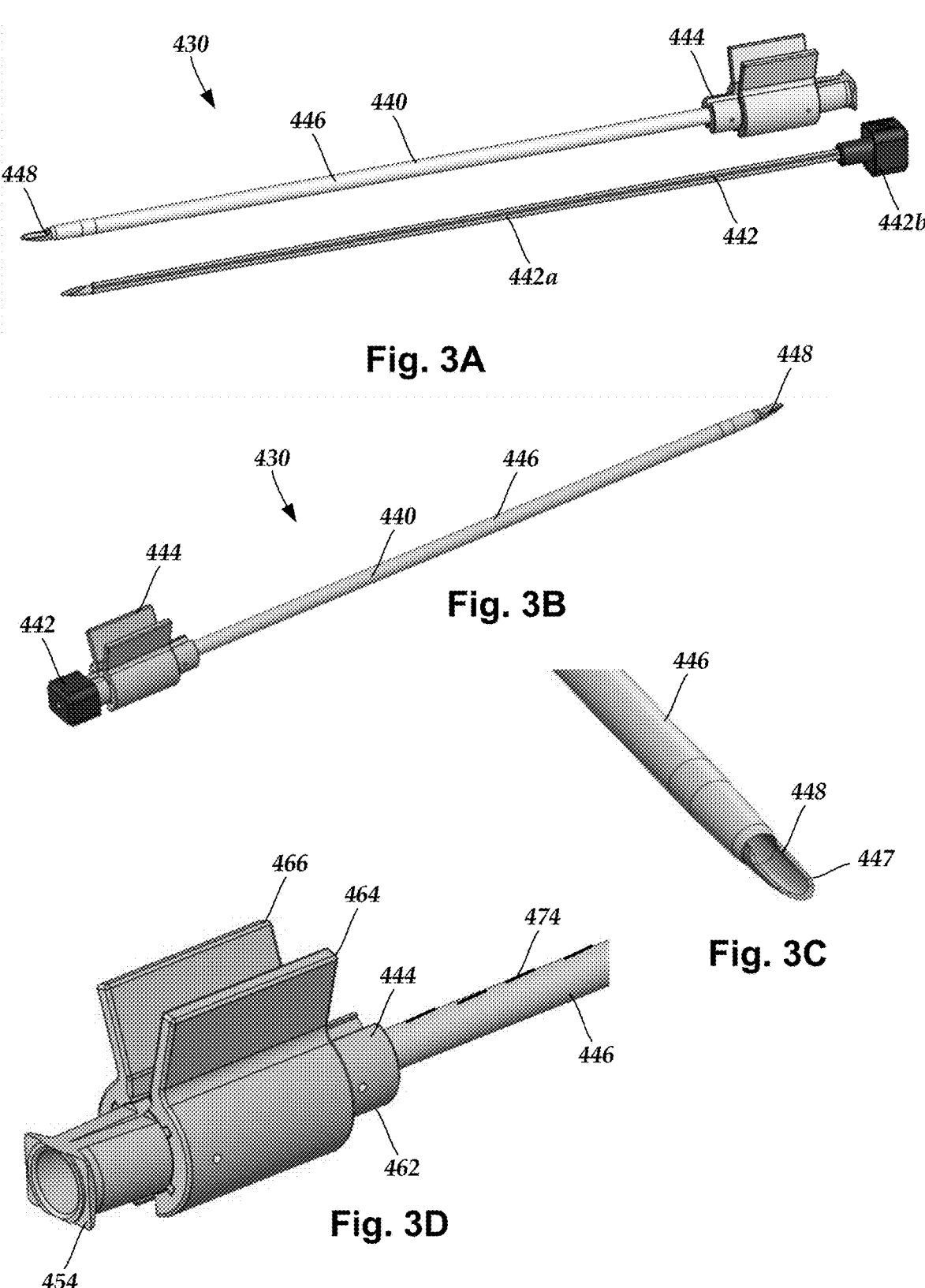
FIG. 3A is a schematic perspective view of one embodiment of a two component lead introducer configured for facilitating implantation of a lead of an electrical stimulation system into a patient, the lead introducer including a combined needle/sheath and a stylet.
FIG. 3B is a schematic perspective view of the lead introducer of FIG. 3A with the stylet inserted into the combined needle/sheath.
FIG. 3C is a schematic perspective view of the distal portion of the combined needle/sheath of the lead introducer of FIG. 3A.
FIG. 3D is a schematic perspective view of the proximal portion of the combined needle/sheath of the lead introducer of FIG. 3A.
Figures 4A, 4B, 4C:
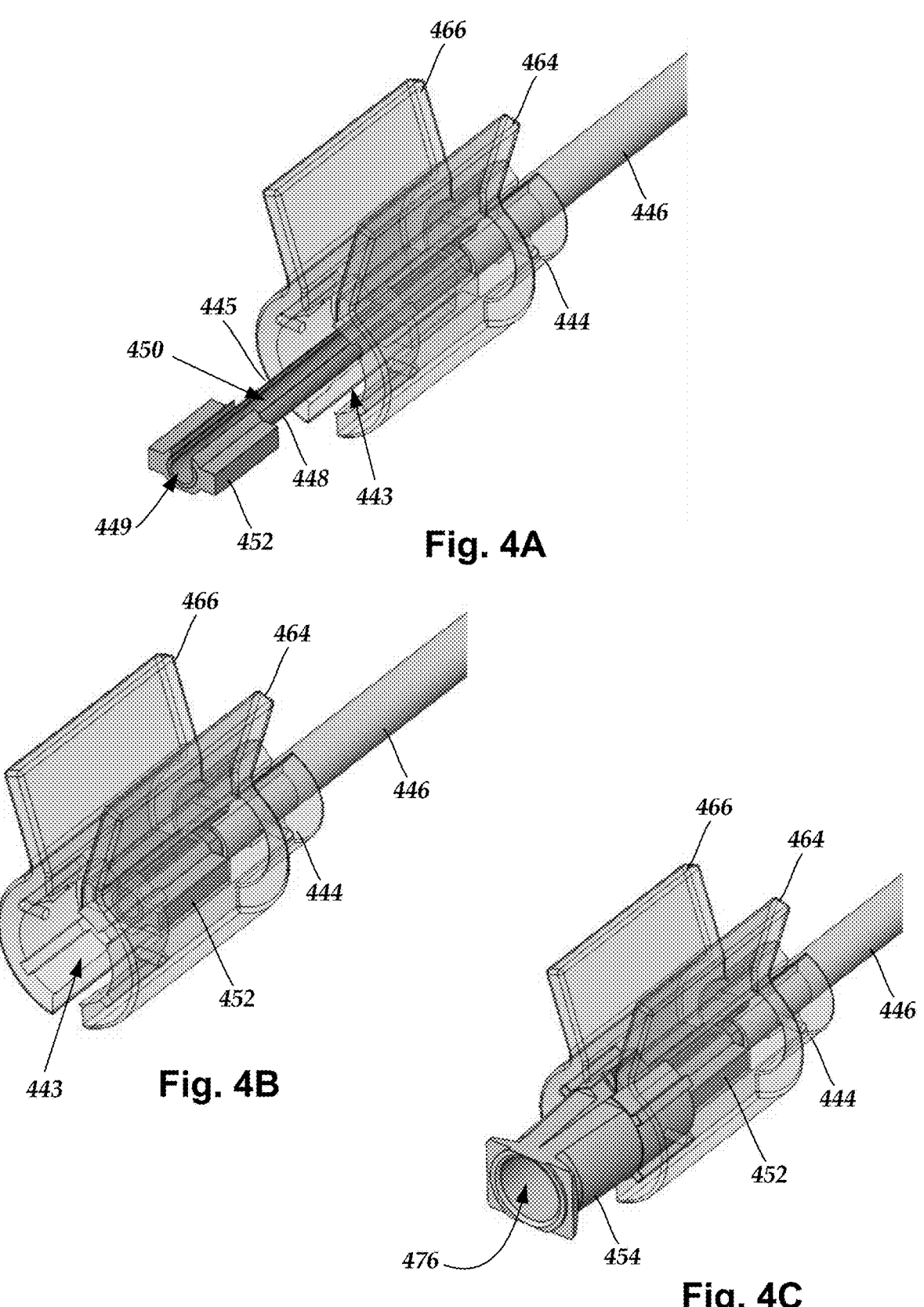
FIG. 4A is a schematic perspective view of the proximal portion of the combined needle/sheath of the lead introducer of FIG. 3A with the needle partially pulled out of the splittable hub.
FIG. 4B is a schematic perspective view of the proximal portion of the combined needle/sheath of the lead introducer of FIG. 3A with the needle inserted into the splittable hub.
FIG. 4C is a schematic perspective view of the proximal portion of the combined needle/sheath of the lead introducer of FIG. 3A with the needle and splittable luer inserted into the splittable hub.
Figure 5A:
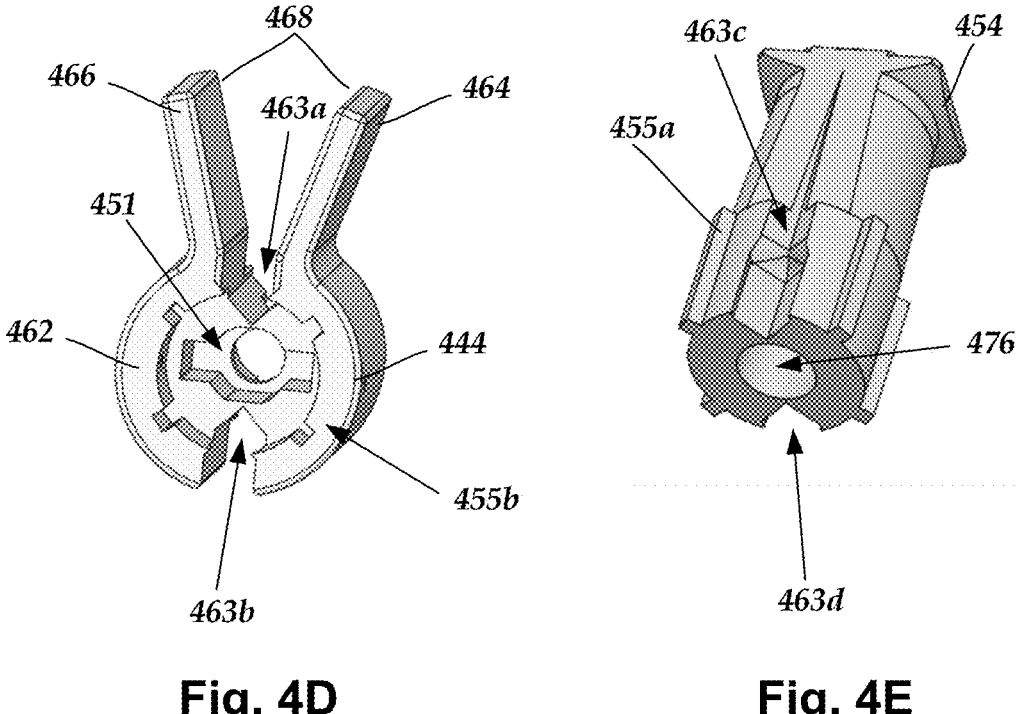
FIG. 5A is a schematic perspective view of one embodiment of a two component lead introducer configured for facilitating implantation of a lead of an electrical stimulation system into a patient, the lead introducer including a splittable needle and a stylet.
Figure 5A:
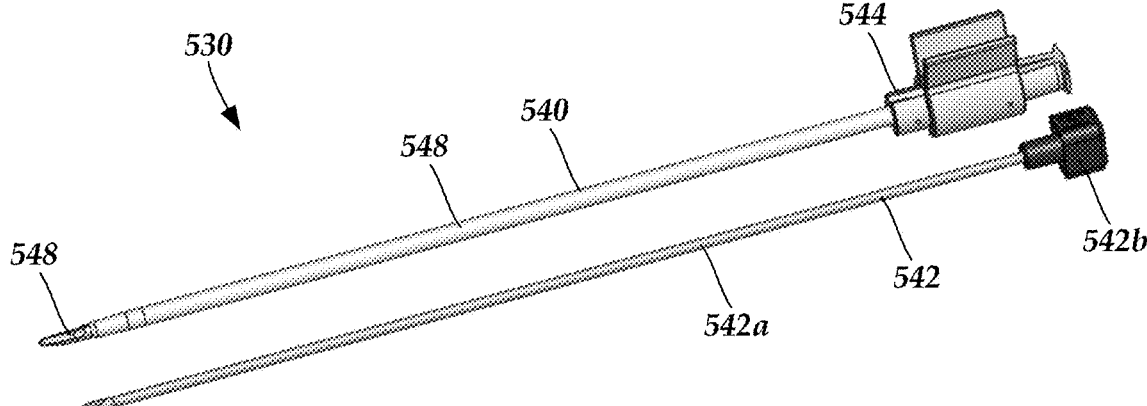
Figures 5B, 5C, 5D:
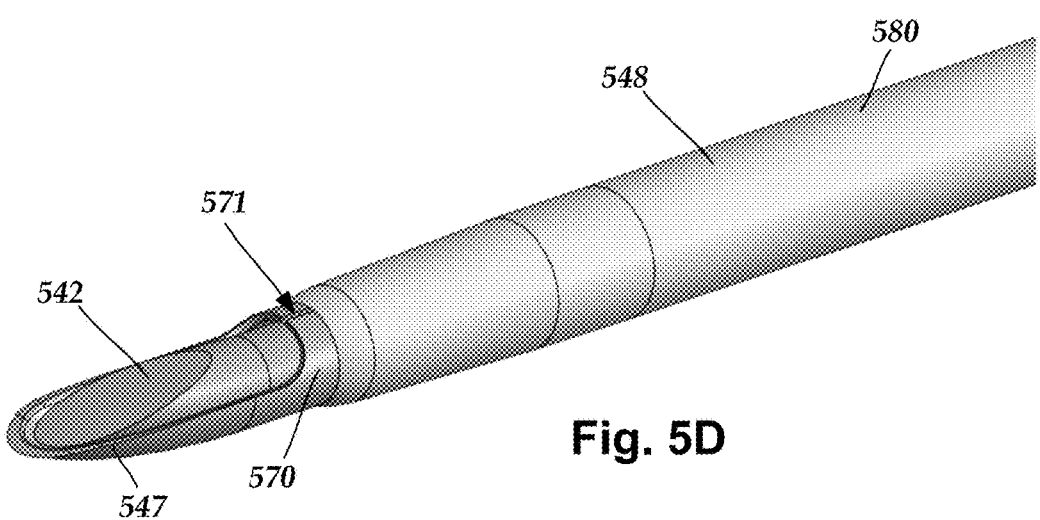
FIG. 5B is a schematic perspective view of the lead introducer of FIG. 5A with the stylet inserted into the splittable needle.
FIG. 5C is a schematic perspective view of the distal portion of the splittable needle of the lead introducer of FIG. 5A with a fluid-resistant coating or liner on the splittable needle being translucent.
FIG. 5D is a schematic perspective view of the distal portion of the splittable needle of the lead introducer of FIG. 5A with the fluid-resistant coating or liner on the splittable needle and the stylet inserted into the splittable needle.

The needle 448 can be made from any suitable material including, but not limited to, stainless steel or other metal. The needle 448 of the combined needle/sheath 440 includes a proximal end portion 445 (FIG. 4B) and a distal end portion 447 (FIG. 3C). FIG. 3C illustrates the distal end portion 447 of the needle 448 extending out of the splittable sheath 446. The distal end portion 447 of the needle 448 may have a slanted face with a sharpened end suitable for piercing patient tissue during insertion of the lead introducer 430 into the patient. At least the sharpened end of the needle 448, and preferably the slanted face, extends distally beyond the distal end of the splittable sheath 446. In other embodiments, the distal end portion 447 of the needle 448 may have a Tuohy tip or blunt epidural tip. An optional bend can be provided along the distal end portion of the needle 448 such as, for example, the bend disclosed in U.S. Patent Application Publication No. 2016/0317800, incorporated herein by reference in its entirety.

The needle 448 defines a channel 449 (FIG. 4B) that extends along the longitudinal length of the needle for receiving the stylet 442 and the lead. The needle also defines a slot 450 that extends along the longitudinal length of the needle. The splittable sheath 446 covers the slot during insertion of the lead introducer 430 and delivery of the lead. The slot 450 allows for lateral separation of the lead from the needle 448 by laterally passing the lead, initially residing in the channel 449, through the slot. In at least some embodiments, to facilitate lateral separation, the slot 450 is at least as wide as the diameter of the lead. In other embodiments, the lead has a diameter that is larger than the slot 450 of the needle 448. The body of the lead may be formed from a deformable material and the lead is removable from the channel 449 by applying a lateral force to at least one of the lead or the needle 448 to deform the lead enough to enable the lead to be passed laterally out through the slot 450 in the needle 448. The splittable hub 444 includes a hub lumen 443 that is in communication with the channel 449 of the needle 448. The splittable luer 454 includes a luer lumen 476 that is in communication with the channel 449 of the needle 448.

Upon assembly of the combined needle/sheath 440, the proximal end portion 445 of the needle 448 is disposed within the splittable hub 444. In at least some embodiments, the needle 448 is not bonded to the splittable hub 444. A locking fixture 452 is attached to, or part of, the proximal end portion 445 of the needle 448. The splittable hub 444 defines a cavity 451 that is complementary to the locking fixture 452. During assembly of the lead introducer 430, the locking fixture 452, with the attached needle 448, is inserted into the cavity 451. In at least some embodiments, the splittable luer 454 is inserted into the splittable hub 444 to lock the locking fixture 452 within the cavity 451 of the splittable hub 444. Other arrangements or components can be used to lock the locking fixture 452 within the cavity 451 of the splittable hub 444. When locked into the splittable hub 444, the locking fixture 452 prevents, or hinders, rotation of the needle 448 relative to the splittable hub. When locked into the splittable hub 444, the splittable hub and splittable luer 454 prevent, or hinder, translation or axial movement of the needle 448 relative to the splittable hub. In at least some embodiments, using the locking fixture 452 allows an arrangement in which the needle 448 and the locking fixture 452 are not bonded to the splittable hub 444.

In at least some embodiments, the locking fixture 452 includes one or more features that provide a non-cylindrical cross-section to the combination of the locking fixture 452 and the proximal end portion 445 of the needle 448. For example, the locking fixture 452 of the illustrated embodiment includes one or more wings 453 that extend away from a cylindrical part of the proximal end portion 445 of the needle 448. In other embodiments, the locking fixture 452 can include any other suitable features that can be used to fix the needle 448 within the splittable hub or provide a non-cylindrical cross-section to the combination of the locking fixture 452 and the proximal end portion 445 of the needle 448.

In at least some embodiments, the locking fixture 452 or proximal end portion 445 of the needle 448 is bonded using glue or other adhesive to the splittable hub 444 or the splittable luer 454, but not to the splittable sheath 446. In at least some embodiments, the combined needle/sheath 440 does not include a locking fixture 452 or corresponding cavity 451 in the splittable hub 444, but the proximal end portion 445 of the needle is bonded using glue or other adhesive to the splittable hub 444 or the splittable luer 454, but not to the splittable sheath 446. In at least some of these embodiments using glue or other adhesive, the locking fixture 452 or proximal end portion 445 of the needle 448 is bonded to the splittable luer 454, but not to the splittable sheath 446 or the splittable hub 444. In at least some embodiments using glue or other adhesive for bonding the proximal end portion 445 of the needle 448 or locking fixture 452 to the splittable hub 444 or the splittable luer 454, when the splittable hub or splittable luer is split into two portions, the bond made by the glue or other adhesive to at least one of these portions is broken and the needle is detached from one (or, in some embodiments, both) of the portions of the splittable hub or splittable luer.

In at least some embodiments, a portion of the splittable luer 454 fits relatively snugly into the splittable hub 444 to lock the locking fixture 452 within the splittable hub. In at least some embodiments, when inserted into the splittable hub 444, the splittable luer 454 forms a friction fit that resists withdrawal of the splittable luer from the splittable hub. In at least some embodiments, the splittable hub 444 and splitable luer include any suitable known coupling or locking arrangement for retaining the splittable luer in the splittable hub.

In at least some embodiments, the splittable luer 454 includes one or more first locating features 455a that engage one or more second locating features 455b of the splittable hub 444. In the illustrated embodiment, the first locating features 455a of the splittable luer 454 are rails and the second locating features 455b of the splittable hub 444 are corresponding notches. In at least some embodiments, the first and second locating features 455a, 455b facilitate splitting of the splittable luer 454 in conjunction with the splitting of the splittable hub 444 using the pull-apart tabs 464, 466 by retaining portions of the splittable luer with respective portions of the splittable hub. In at least some embodiments, the splittable luer 454 and locking fixture 452 can be a single unit.

In at least some embodiments, in operation, the stylet 442 is received in the channel 449 during insertion. The stylet 442 is withdrawn along the channel 449 and the lead is inserted. After positioning the lead at, or near, the desired implantation site, the splittable hub 444, splittable sheath 446, and splittable luer 454, when present, are split and then removed. The needle 448 is removed from the patient with the lead passing through the slot 450 to remain implanted.

FIGS. 5A to 5D illustrate a two component lateral release lead introducer 530 having a splittable needle arrangement 540 and a stylet 542. The stylet 542 includes a shaft 542a and a handle 542b. The shaft 542a of the stylet 542 is inserted into the splittable needle arrangement 540 and the combination is inserted into the patient. After insertion and location of the lead introducer 530 at or near the implant site, the stylet 542 is removed from the splittable needle arrangement 540 and a lead is inserted into the splittable needle arrangement 540 for delivery and placement of the lead at the implant site.

The splittable needle arrangement 540 includes a splittable hub 544 and a splittable needle 548. The splittable needle 548 can include a needle shaft 570 that, for example, is perforated, etched, stamped, scored, or grooved or includes two portions that are tack or spot welded along the needle for temporary joining of the two portions.

The splittable needle 548 can be made from any suitable material including, but not limited to, stainless steel or other metal. The distal end portion 547 of the splittable needle 548 may have a slanted face with a sharpened end suitable for piercing patient tissue during insertion of the lead introducer 530 into the patient. In other embodiments, the distal end portion 547 of the splittable needle 548 may have a Tuohy tip or blunt epidural tip. An optional bend can be provided along the distal end portion of the splittable needle 548 such as, for example, the bend disclosed in U.S. Patent Application Publication No. 2016/0317800, incorporated herein by reference in its entirety.

The splittable hub 544 can be the same as the splittable hub 444 described above except that the splittable hub 544 is bonded to the splittable needle 548. When the splittable hub 544 is split into two portions, the splittable needle 548 is also split into two portions with each portion of the splittable hub being attached to a corresponding portion of the splittable needle. The splittable hub 544 can include two pull-apart tabs 564, 566 that are the same or similar to the two pull-apart tabs 464, 466 described above. The splittable hub 544 can include one or more of the slits or weakened regions 563 that are the same or similar to the slits or weakened regions 463*a*, 463*b* described above.

In at least some embodiments, the splittable needle 548 includes a fluid-resistant coating or liner 580 disposed over at least a portion of the interior or exterior surface of the needle shaft 570 of the splittable needle. The fluid-resistant coating or liner 580 is translucent in FIG. 5C for illustration of the needle shaft 570. In at least some embodiments, the fluid-resistant coating or liner 580 is disposed over the portion of the interior or exterior surface of the needle shaft 570 of the splittable needle 548 that includes at least a portion of the seam(s) 571 where the splittable needle will be split, for example, over the perforations, scoring, grooves, welded regions, or the like. In at least some embodiments, the fluid-resistant coating or liner 580 is disposed over a portion of the interior or exterior surface of an entirety of at least the portion of the splittable needle 548 that is inserted into the patient (optionally, excluding the tip of the splittable needle or the distal end portion of the splittable needle). The fluid-resistant coating or liner 580 can be disposed over the interior or exterior surface or both the exterior and interior surface.

Examples of materials for the fluid-resistant coating or liner 580 include, but are not resistant to, biocompatible polymers, such as, for example, silicone, polyurethane, polyetheretherketone (PEEK), or the like, or a biocompatible adhesive or glue such as, for example, biocompatible epoxy, or the like, or any combination thereof. A fluid-resistant coating or liner 580 can be formed on the splittable needle 548 using dip coating; heat shrinking; application of polymer, adhesive, or glue; or any other suitable method.

Figure 6:
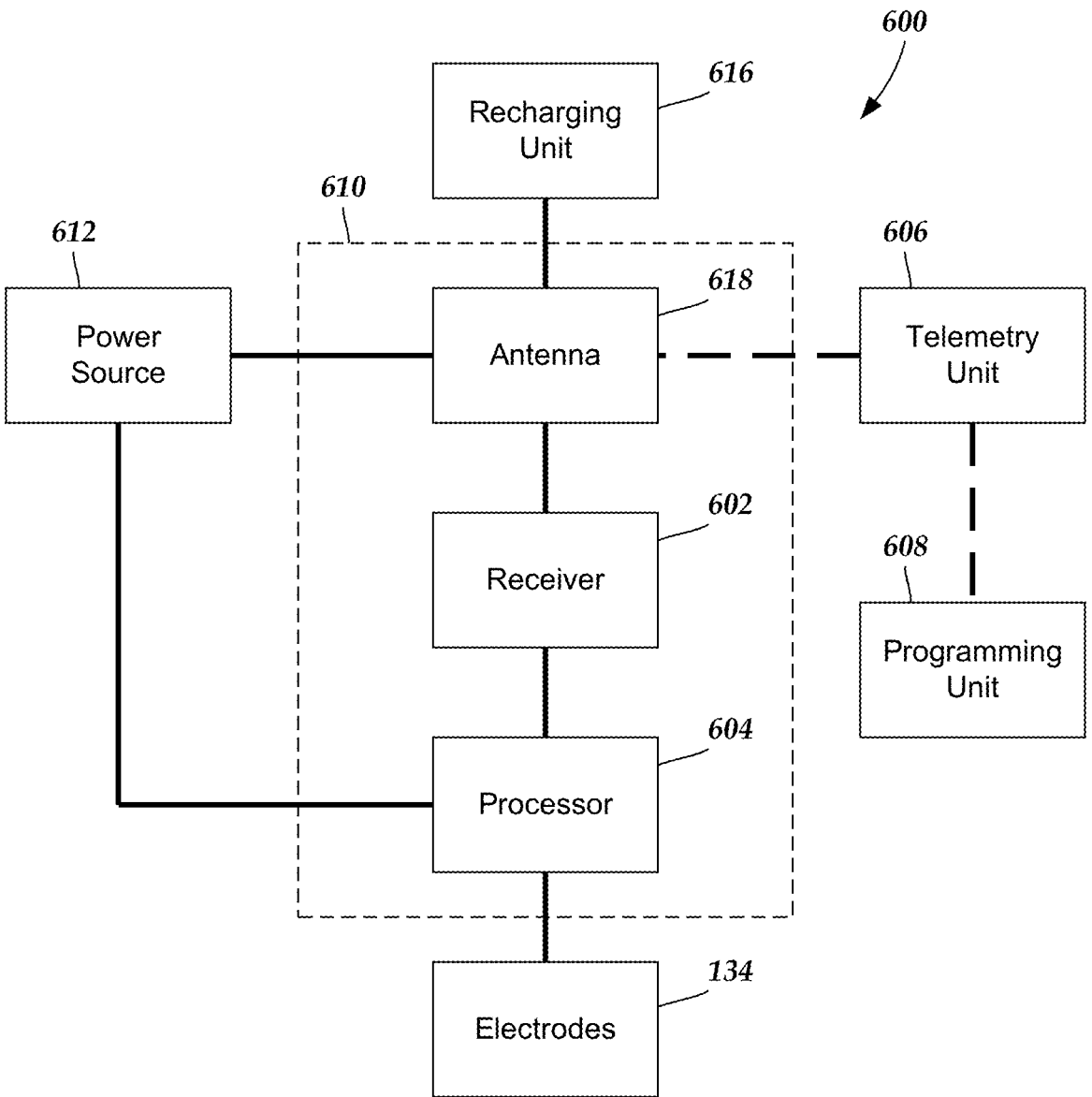
FIG. 6 is a schematic overview of one embodiment of components of a stimulation system, including an electronic subassembly disposed within a control module, according to the invention.

FIG. 6 is a schematic overview of one embodiment of components of an electrical stimulation system 600 including an electronic subassembly 610 disposed within a control module. It will be understood that the electrical stimulation system can include more, fewer, or different components and can have a variety of different configurations including those configurations disclosed in the stimulator references cited herein.

Some of the components (for example, power source 612, antenna 618, receiver 602, and processor 604) of the electrical stimulation system can be positioned on one or more circuit boards or similar carriers within a sealed housing of an implantable pulse generator, if desired. Any power source 612 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 6,437,193, incorporated herein by reference in its entirety.

As another alternative, power can be supplied by an external power source through inductive coupling via the optional antenna 618 or a secondary antenna. The external power source can be in a device that is mounted on the skin of the user or in a unit that is provided near the user on a permanent or periodic basis.

If the power source 612 is a rechargeable battery, the battery may be recharged using the optional antenna 618, if desired. Power can be provided to the battery for recharging by inductively coupling the battery through the antenna to a recharging unit 616 external to the user. Examples of such arrangements can be found in the references identified above.

In one embodiment, electrical current is emitted by the electrodes 134 on the lead body to stimulate nerve fibers, muscle fibers, or other body tissues near the electrical stimulation system. A processor 604 is generally included to control the timing and electrical characteristics of the electrical stimulation system. For example, the processor 604 can, if desired, control one or more of the timing, frequency, amplitude, width, and waveform of the pulses. In addition, in at least some embodiments, the processor 604 can select which electrodes can be used to provide stimulation, if desired. In some embodiments, the processor 604 may select which electrode(s) are cathodes and which electrode(s) are anodes. In some embodiments, the processor 604 may be used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 608 that, for example, allows modification of pulse characteristics. In the illustrated embodiment, the processor 604 is coupled to a receiver 602 which, in turn, is coupled to the optional antenna 618. This allows the processor 604 to receive instructions from an external source to, for example, direct the pulse characteristics and the selection of electrodes, if desired.

In one embodiment, the antenna 618 is capable of receiving signals (e.g., RF signals) from an external telemetry unit 606 which is programmed by a programming unit 608. The programming unit 608 can be external to, or part of, the telemetry unit 606. The telemetry unit 606 can be a device that is worn on the skin of the user or can be carried by the user and can have a form similar to a pager, cellular phone, or remote control, if desired. As another alternative, the telemetry unit 606 may not be worn or carried by the user but may only be available at a home station or at a clinician's office. The programming unit 608 can be any unit that can provide information to the telemetry unit 606 for transmission to the electrical stimulation system 600. The programming unit 608 can be part of the telemetry unit 606 or can provide signals or information to the telemetry unit 606 via a wireless or wired connection. One example of a suitable programming unit is a computer operated by the user or clinician to send signals to the telemetry unit 606.

The signals sent to the processor 604 via the antenna 618 and receiver 602 can be used to modify or otherwise direct the operation of the electrical stimulation system. For example, the signals may be used to modify the pulses of the electrical stimulation system such as modifying one or more of pulse width, pulse frequency, pulse waveform, and pulse amplitude. The signals may also direct the electrical stimulation system 600 to cease operation, to start operation, to start charging the battery, or to stop charging the battery. In other embodiments, the stimulation system does not include an antenna 618 or receiver 602 and the processor 604 operates as programmed.

Optionally, the electrical stimulation system 600 may include a transmitter (not shown) coupled to the processor 604 and the antenna 618 for transmitting signals back to the telemetry unit 606 or another unit capable of receiving the signals. For example, the electrical stimulation system 600 may transmit signals indicating whether the electrical stimulation system 600 is operating properly or not or indicating when the battery needs to be charged or the level of charge remaining in the battery. The processor 604 may also be capable of transmitting information about the pulse characteristics so that a user or clinician can determine or verify the characteristics.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected is:

1. A lead introducer comprising:
a combined needle/sheath comprising
 a splittable sheath having a length and a proximal end region and configured to split along the length of the splittable sheath into a first portion and a second portion,
 a splittable hub coupled to the proximal end region of the splittable sheath and configured to split into a first portion and a second portion, and
 a needle arrangement consisting of
 a needle having a length and a proximal end region, the needle defining a channel extending along the length of the needle for delivery of a lead through the needle, wherein the needle is configured to extend through the splittable hub and the splittable sheath, wherein the needle is not bonded to the splittable hub and the splittable sheath, and
 a non-cylindrical locking fixture attached to, or part of, the proximal end region of the needle,
 wherein the splittable hub comprises a cavity having a shape complementary to the non-cylindrical locking fixture of the needle arrangement to hold at least a portion of the proximal end region of the needle and an entirety of the non-cylindrical locking fixture within the splittable hub and restrict rotation of the needle relative to the splittable hub.

2. The lead introducer of claim 1, wherein the combined needle/sheath further comprises a splittable luer configured for insertion into the splittable hub to lock the non-cylindrical locking fixture of the needle arrangement within the cavity of the splittable hub, wherein the splittable luer is configured to split into a first portion and a second portion.

3. The lead introducer of claim 2, wherein the needle is not bonded to the splittable luer.

4. The lead introducer of claim 2, wherein the splittable hub and the splittable luer comprise complementary locating features to facilitate simultaneous splitting of the splittable hub and the splittable luer.

5. The lead introducer of claim 1, wherein the non-cylindrical locking fixture comprises at least one wing.

6. The lead introducer of claim 1, wherein the splittable hub comprises a body and at least two tabs extending from the body, wherein the splittable hub is configured to be split, along with the splittable sheath, using the at least two tabs.

7. The lead introducer of claim 1, wherein the needle defines a slot along the length of the needle configured for lateral release of the lead from the channel of the needle.

8. The lead introducer of claim 1, further comprising a stylet configured for insertion into the channel of the needle.

9. The lead introducer of claim 1, wherein the first portion of the splittable sheath is permanently attached to the first portion of the splittable hub so that when the splittable hub is split into the first and second portions, the first portion of the splittable sheath remains attached to the first portion of the splittable hub.

10. The lead introducer of claim 1, wherein the splittable hub comprises at least one slit or weakened region for splitting the splittable hub into the first and second portions.

11. An insertion kit comprising:
 the lead introducer of claim 1; and
 the lead configured for implantation into a patient, the lead comprising
 a lead body having a distal end portion and a proximal end portion,
 a plurality of electrodes disposed at the distal end portion of the lead body,
 a plurality of terminals disposed at the proximal end portion of the lead body, and
 a plurality of conductive wires coupling the electrodes electrically to the terminals;
 wherein the lead is insertable through the channel of the needle.

12. A lead introducer comprising:
a combined needle/sheath comprising
 a splittable sheath having a length and a proximal end region and configured to split along the length of the splittable sheath into a first portion and a second portion,
 a splittable hub coupled to the proximal end region of the splittable sheath and configured to split into a first portion and a second portion,
 a needle having a length and a proximal end region, the needle defining a channel extending along the length of the needle for delivery of a lead through the needle, wherein the needle is configured to extend through the splittable hub and the splittable sheath, wherein the needle is not bonded to the splittable hub and the splittable sheath, and
 a splittable luer configured for insertion into the splittable hub and adhesively bonded to the needle, wherein the splittable luer is configured to split into a first portion and a second portion breaking the adhesive bond between at least one of the first or second portions of the splittable luer and the needle.

13. The lead introducer of claim 12, wherein the splittable hub and the splittable luer comprise complementary locating features to facilitate simultaneous splitting of the splittable hub and the splittable luer.

14. The lead introducer of claim 12, wherein the splittable hub comprises a body and at least two tabs extending from the body, wherein the splittable hub is configured to be split, along with the splittable sheath and the splittable luer, using the at least two tabs.

15. The lead introducer of claim 12, wherein the splittable hub and the splittable luer comprise complementary locating features to facilitate simultaneous splitting of the splittable hub and the splittable luer.

16. The lead introducer of claim 12, wherein the needle defines a slot along the length of the needle configured for lateral release of the lead from the channel of the needle.

17. The lead introducer of claim 12, further comprising a stylet configured for insertion into the channel of the needle.

18. The lead introducer of claim 12, wherein the first portion of the splittable sheath is permanently attached to the first portion of the splittable hub so that when the splittable hub is split into the first and second portions, the first portion of the splittable sheath remains attached to the first portion of the splittable hub.

19. The lead introducer of claim 12, wherein the splittable hub comprises at least one slit or weakened region for splitting the splittable hub into the first and second portions.

20. An insertion kit comprising:

the lead introducer of claim 12; and the lead configured for implantation into a patient, the lead comprising a lead body having a distal end portion and a proximal end portion, a plurality of electrodes disposed at the distal end portion of the lead body, a plurality of terminals disposed at the proximal end portion of the lead body, and a plurality of conductive wires coupling the electrodes electrically to the terminals;

wherein the lead is insertable through the channel of the needle.

* * * * *